(12) United States Patent
Salgo

(10) Patent No.: US 7,794,398 B2
(45) Date of Patent: Sep. 14, 2010

(54) REAL-TIME VOLUMETRIC BI-PLANE ULTRASOUND IMAGING AND QUANTIFICATION

(75) Inventor: Ivan Salgo, Andover, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 943 days.

(21) Appl. No.: 10/573,068

(22) PCT Filed: Aug. 6, 2004

(86) PCT No.: PCT/IB2004/051416

§ 371 (c)(1),
(2), (4) Date: Mar. 23, 2006

(87) PCT Pub. No.: WO2005/030057

PCT Pub. Date: Apr. 7, 2005

(65) Prior Publication Data

US 2007/0016019 A1 Jan. 18, 2007

Related U.S. Application Data

(60) Provisional application No. 60/507,263, filed on Sep. 29, 2003.

(51) Int. Cl.
*A61B 8/00* (2006.01)
(52) U.S. Cl. .................. 600/443; 600/437; 600/509; 382/128

(58) Field of Classification Search .............. 600/443, 600/447, 440, 450, 508; 382/128, 286; 345/419, 345/619
See application file for complete search history.

(56) References Cited

U.S. PATENT DOCUMENTS

| 5,107,838 | A  | * | 4/1992  | Yamaguchi ............. 600/410 |
| 5,465,721 | A  | * | 11/1995 | Kishimoto et al. ....... 600/443 |
| 6,443,896 | B1 | * | 9/2002  | Detmer .................. 600/445 |
| 6,537,220 | B1 | * | 3/2003  | Friemel et al. .......... 600/447 |
| 2002/0072671 | A1 | * | 6/2002 | Chenal et al. ............ 600/450 |
| 2003/0055308 | A1 | * | 3/2003 | Friemel et al. .......... 600/15 |

FOREIGN PATENT DOCUMENTS

EP 961135 A1 * 12/1999

* cited by examiner

*Primary Examiner*—Brian Casler
*Assistant Examiner*—Parikha S Mehta
(74) *Attorney, Agent, or Firm*—W. Brinton Yorks, Jr.

(57) ABSTRACT

Quantified measures of a volumetric object in the body can be made ultrasonically by acquiring concurrent biplane images of two different image planes of the object. Corresponding borders of the volumetric object are traced using automatic border detection. The border tracings are used in their planar spatial relationship to compute a graphical model of the volumetric object. The volume of the graphical model may be computed by the rule of disks, and a graphical or numerical display of the changing volume with time displayed. A user interface comprises both real time biplane images, the real time graphical model, and the quantified measures.

17 Claims, 10 Drawing Sheets

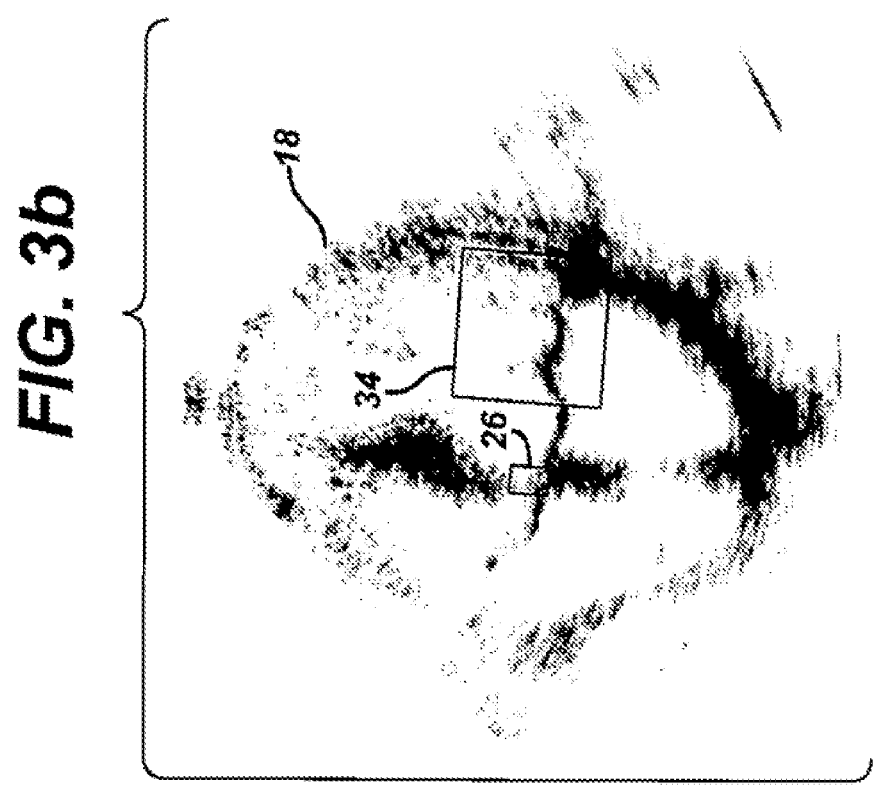
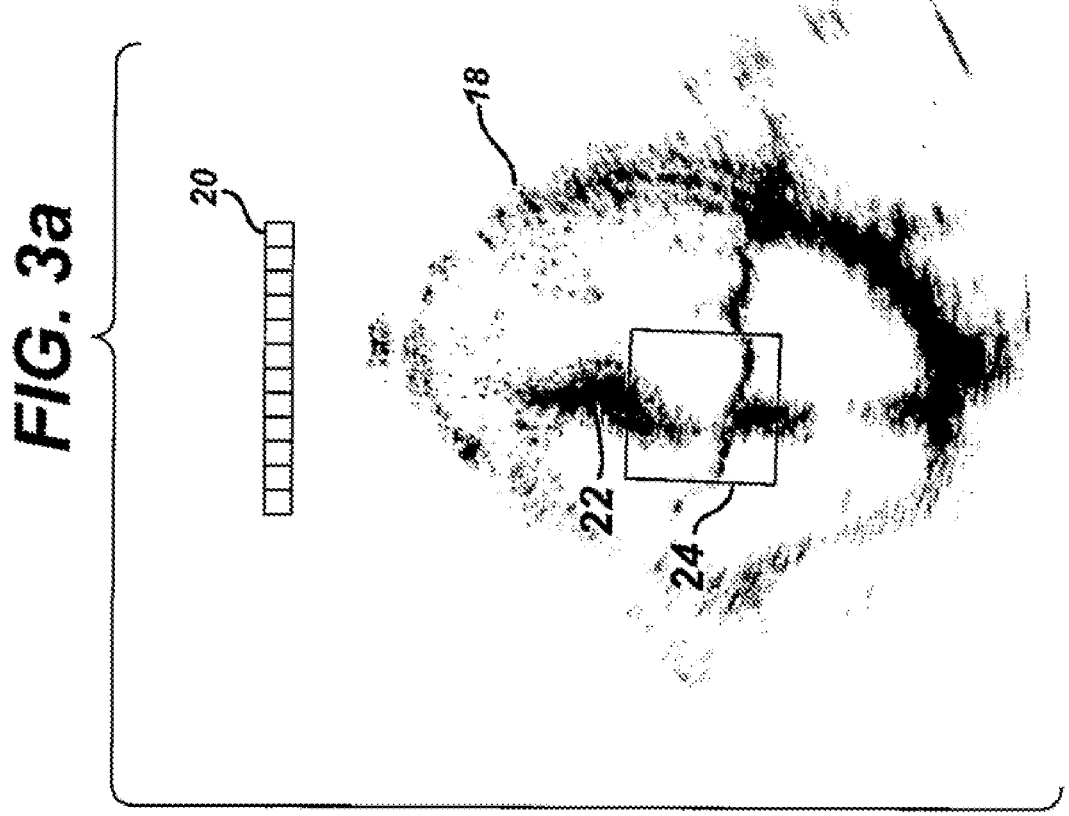

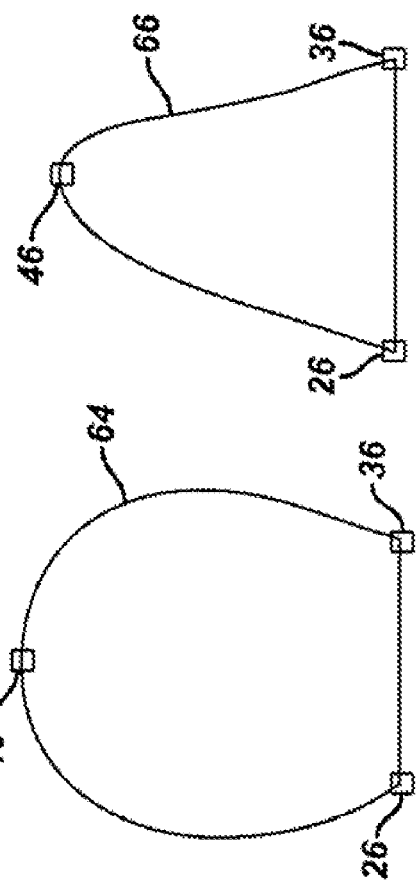
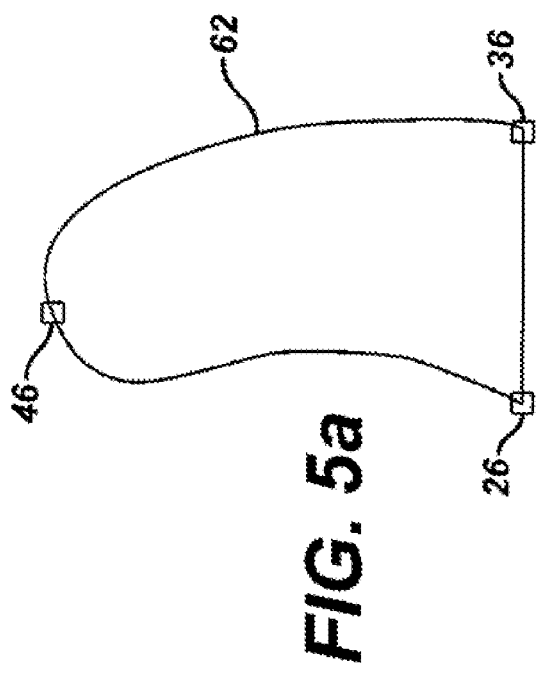
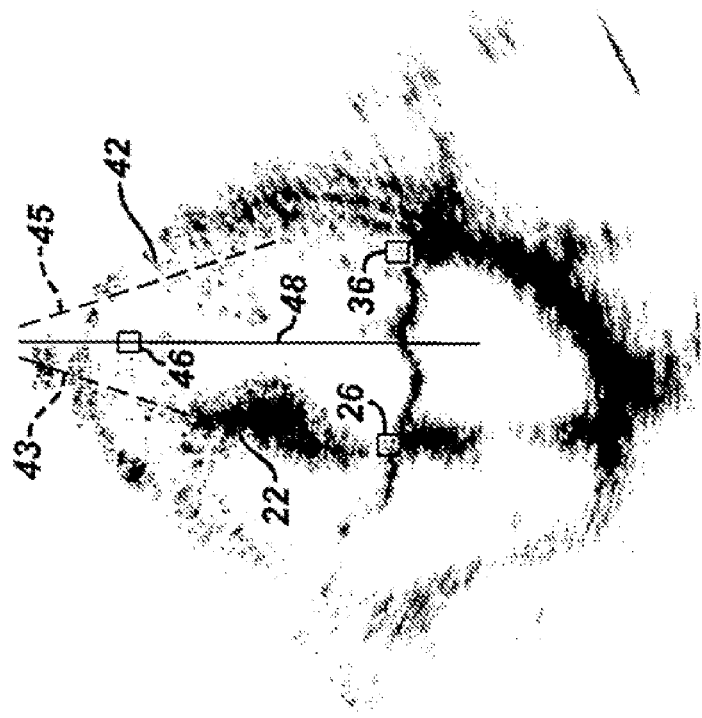

REAL-TIME VOLUMETRIC BI-PLANE ULTRASOUND IMAGING AND QUANTIFICATION

CROSS REFERENCE TO RELATED APPLICATION

This application claims the benefit of U.S. provisional application Ser. No. 60/507,263 filed Sep. 29, 2003, which is incorporated herein.

This invention relates to ultrasonic diagnostic imaging and, more particularly, to ultrasonic imaging systems capable of estimating the volume of vessels and organs such as the heart.

Echocardiographic ultrasonic imaging systems are used to assess the performance of the heart. Cardiac performance can be assessed qualitatively with these systems, such as by observing the blood flow through vessels and valves and the operation of heart valves. Quantitative measures of cardiac performance can also be obtained with such systems. For instance, the velocity of blood flow and the sizes of organs and cavities such as a heart chamber can be measured. These measures can produce quantified values of cardiac performance such as ejection fraction and cardiac output. A method and apparatus for measuring the volume of a heart chamber are described in U.S. Pat. No. 5,322,067 (Prater et al.), for example. In the method described in this patent, the clinician acquires a sequence of ultrasound images of a cavity to be measured, such as the left ventricle of the heart. The clinician freezes one of the images on the display screen and traces a fixed region of interest (ROI) around the cavity of the heart chamber. The defined ROI should be large enough to encompass the heart chamber when the heart is fully expanded. The ultrasound system then processes the pixels in the ROI in each image in the sequence to determine those pixel that are blood pixels in the left ventricle. Each left ventricle is then segmented into strips and the area of the strips is calculated. Each strip is then conceptually rotated about its center to define a disk and the volume of each disk is calculated. By summing the volumes of the disks in each image the volume of the heart chamber is determined at each point in the heart cycle for which an image was acquired. The calculated volumes can be displayed numerically as a function of time, or a waveform representative of left ventricle volume as a function of time can be produced, thereby showing the clinician the changes in left ventricular volume over the heart cycle.

The method of the Prater et al. patent requires manual input from the clinician who must define the ROI by a manual tracing. The method can only be performed on a stored image loop due to this need for manual input. It would be desirable for such a technique to be performed by the ultrasound system automatically and to be performed in true real time as the images are acquired. Furthermore, the method of disks (Simpson's rule) volume estimation assumes that each disk is uniformly circular, which may not be the case. It would be desirable to estimate cavity volumes that are more closely related to the true shape of the anatomy rather than having to rely on an assumption of geometric uniformity of the anatomy, thus producing more accurate volume measures.

In accordance with the principles of the present invention, the volume of a body cavity or organ is measured by ultrasonic imaging. Cross-sectional images in different planes of the body cavity are acquired at substantially the same time, thus presenting views of the shape of the cavity at a point in time from different perspectives. A surface of the cavity or organ in each image is outlined by automated or semi-automated border tracing. Segments of the cavity are defined by producing a geometric model of the cavity or organ from the tracings. The segment volumes are accumulated to produce an accurate measure of the volume of the cavity. The inventive method can be performed in real time and produces a more accurate estimate of the cavity volume. The resulting measure can be displayed numerically or as a physiologic curve of the changing volume with time.

In the drawings:

FIGS. 3a and 3b illustrate the step of locating the medial mitral annulus (MMA) and the lateral mitral annulus (LMA) in an ultrasound image of the left ventricle (LV).

FIG. 4 illustrates the step of locating the apex of the LV.

FIGS. 5a-5c illustrate standard border shapes for the LV.

Figure 1:
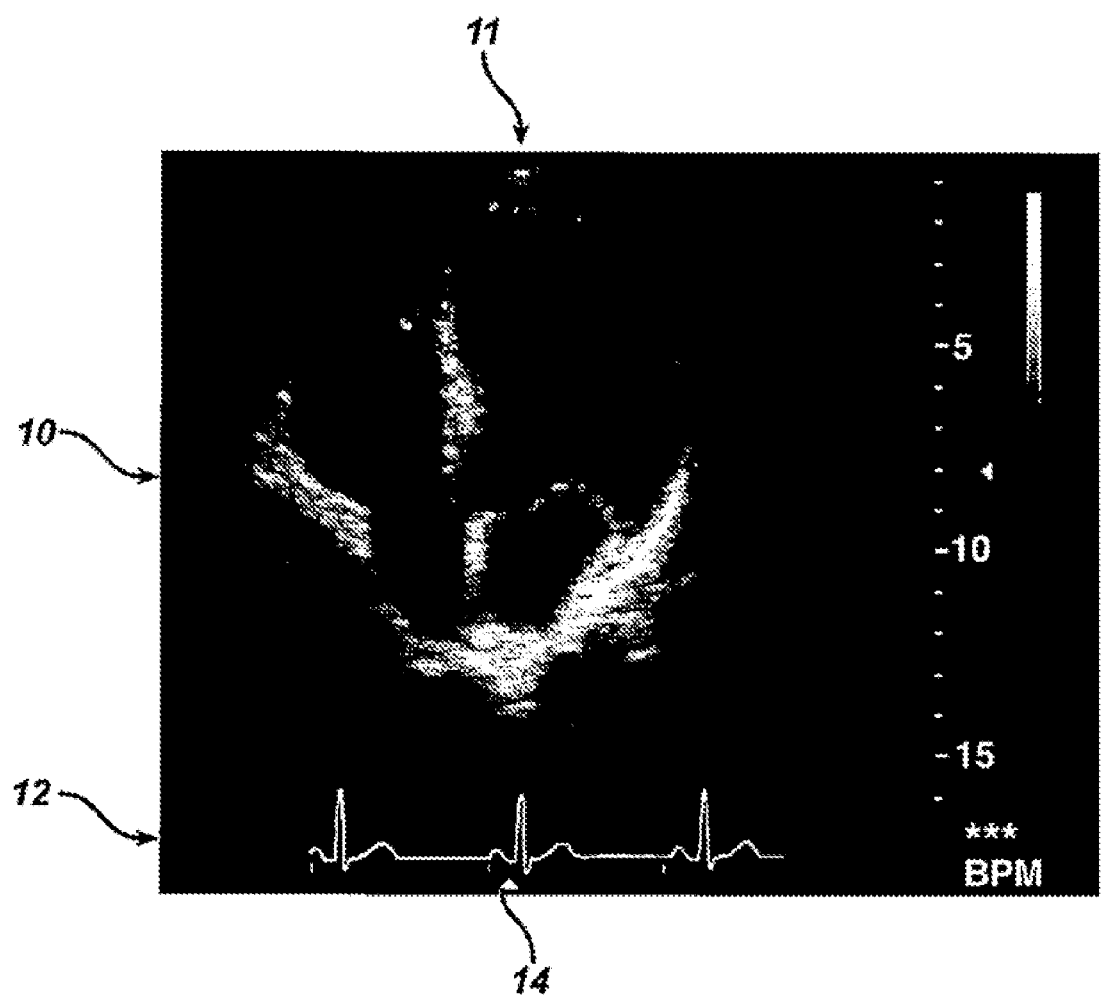
FIG. 1 is a four chamber ultrasound image of the heart.

Referring first to FIG. 1, an ultrasound system display is shown during the acquisition of cardiac images. The ultrasound image 10 is a four-chamber view of the heart which is acquired by a phased array transducer probe to produce the illustrated sector-shaped image. The image shown is one of a sequence of real-time images acquired by placement of the probe for an apical 4-chamber view of the heart, in which the probe is oriented to view the heart from the proximity of its apex 11. The largest chamber in the image, in the central and upper right portion of the image, is the left ventricle (LV). As the real-time ultrasound image sequence is acquired a scrolling ECG trace 12 of the heart cycle is simultaneously acquired and displayed at the bottom of the display, with a triangular marker 14 denoting the point or phase of the cardiac cycle at which the currently-displayed image was acquired. A typical duration of the heart cycle when the body is at rest is about one second, during which time approximately 30-90 image frames of the heart can be acquired and displayed in rapid succession. As the clinician views the display of FIG. 1, the heart is seen beating in real time in the ultrasound display as the ECG waveform 12 scrolls beneath the ultrasound images 10, with the instantaneously displayed heart phase indicated by the marker 14.

In one mode of acquisition, the clinician observes the beating heart in real time while manipulating the transducer probe so that the LV is being viewed distinctly in maximal cross-section. When the four chamber view is being acquired continuously and clearly, the clinician depresses the "freeze" button to retain the images of the current heart cycle in the image frame or Cineloop® memory of the ultrasound system. The Cineloop memory will retain all of the images in the memory at the time the freeze button is depressed which, depending upon the size of the memory, may include the loop being viewed at the time the button was depressed as well as images of a previous or subsequent loop. A typical Cineloop memory may hold 400 image frames, or images from about eight to ten heart cycles. The clinician can then scan through the stored images with a trackball, arrow key, or similar control to select the loop with the images best suited for analysis. When the clinician settles on a particular loop, the "ABD" protocol is actuated to start the border drawing process.

Figure 2:
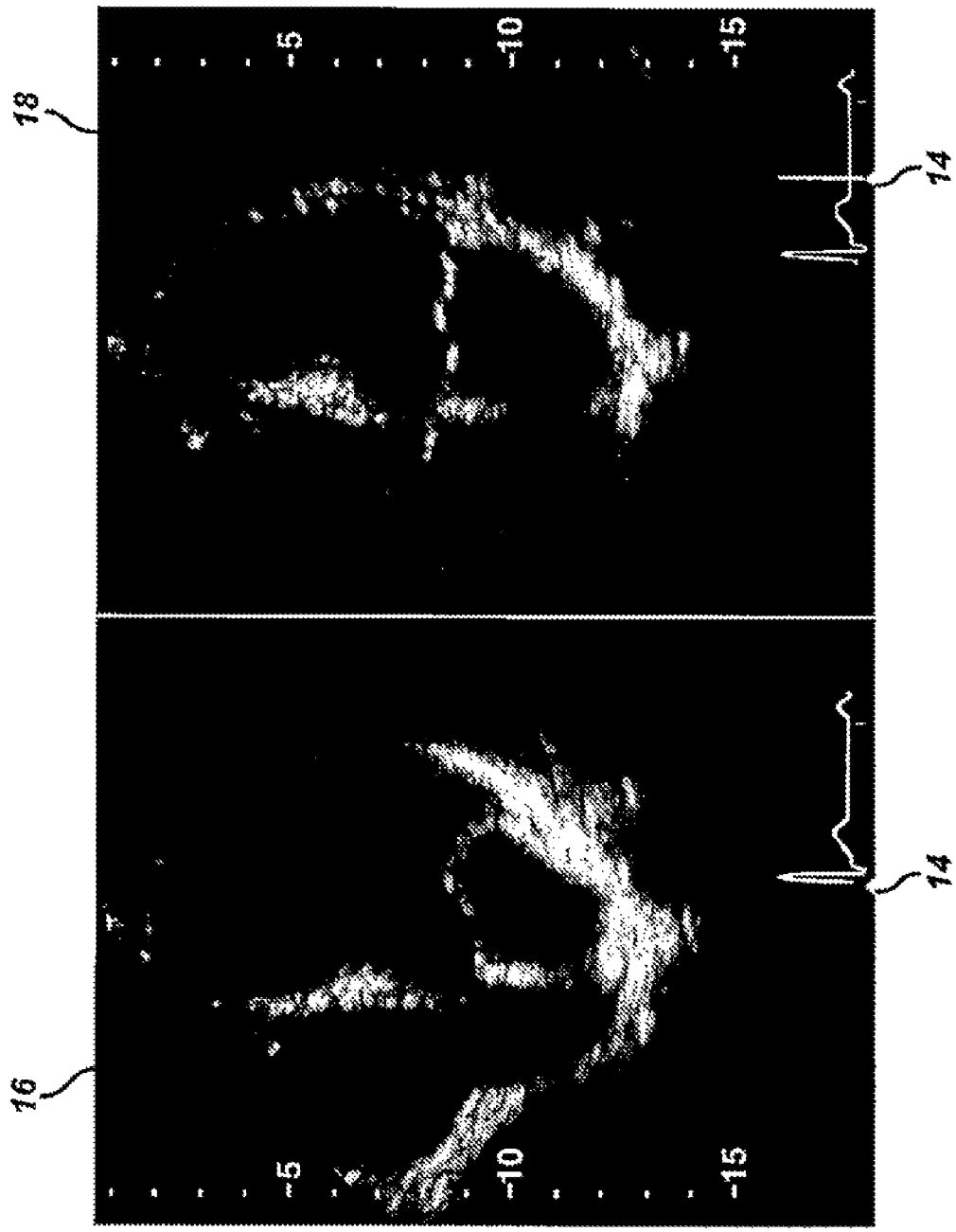
FIG. 2 illustrates an ultrasound display of both end diastole and end systole cardiac images.

When the ABD protocol is actuated the display changes to a dual display of the end diastole image 16 and the end systole image 18 displayed side-by-side as shown in FIG. 2. The ultrasound system identifies all of the images comprising the selected loop by the duration of the ECG waveform associated with the selected loop. The ultrasound system also recognizes the end diastole and end systole points of the cardiac cycle in relation to the R-wave of the ECG waveform 12 and thus uses the ECG waveform R-wave to identify and display the ultrasound images at these two phases of the heart cycle. The dual display of FIG. 2 shows the ECG waveform 12 for the selected heart cycle beneath each ultrasound image, with the marker 14 indicating the end diastole and end systole phases at which the two displayed images were acquired.

Since the Cineloop memory retains all of the images of the cardiac cycle, the user has the option to review all of the images in the loop, including those preceding and succeeding those shown in the dual display. For instance, the clinician can "click" on either of the images to select it, then can manipulate the trackball or other control to sequentially review the images which precede or succeed the one selected by the ultrasound system. Thus, the clinician can select an earlier or later end diastole or end systole image from those selected by the ultrasound system. When the clinician is satisfied with the displayed images 16 and 18, the ABD processor is actuated to automatically delineate the LV borders on the two displayed images as well as the intervening undisplayed images between end diastole and end systole.

In this example the ABD processor begins by drawing the endocardial border of the LV in the end systole image 18. The first step in drawing the border of the LV is to locate three key landmarks in the image, the medial mitral annulus (MMA), the lateral mitral annulus (LMA), and the endocardial apex. This process begins by defining a search area for the MMA as shown in FIG. 3a, in which the ultrasound image grayscale is reversed from white to black for ease of illustration. Since the ABD processor is preconditioned in this example to analyze four-chamber views of the heart with the transducer 20 viewing the heart from its apex, the processor expects the brightest vertical nearfield structure in the center of the image to be the septum which separates the left and right ventricles. This means that the column of pixels in the image with the greatest total brightness value should define the septum. With these cues the ABD processor locates the septum 22, and then defines an area in which the MMA should be identified. This area is defined from empirical knowledge of the approximate depth of the mitral valve from the transducer in an apical view of the heart. A search area such as that enclosed by the box 24 in FIG. 3a is defined in this manner.

Figure 6A:
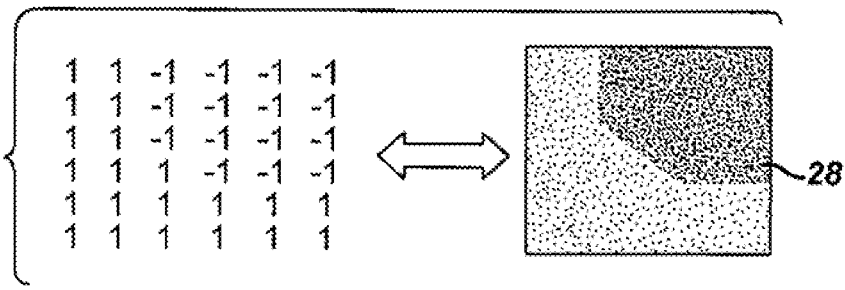
FIGS. 6a-6b illustrate geometric templates used to locate the MMA and LMA.

In this embodiment a filter template defining the anticipated shape of the MMA is then cross correlated to the pixels in the MMA search area. While this template may be created from expert knowledge of the appearance of the MMA in other four-chamber images as used by Wilson et al. in their paper "Automated analysis of echocardiographic apical 4-chamber images," Proc. of SPIE, August, 2000, a geometric corner template may be used as follows. While a right-angle corner template may be employed, in a constructed embodiment an octagon corner template 28 (the lower left corner of an octagon) is used as the search template for the MMA, as shown at the right side of FIG. 6a. In practice, the octagon template is represented by the binary matrix shown at the left side of FIG. 6a. The ABD processor performs template matching by cross correlating different sizes of this template with the pixel data in different translations and rotations until a maximum correlation coefficient above a predetermined threshold is found. To speed up the correlation process, the template matching may initially be performed on a reduced resolution form of the image, which highlights major structures and may be produced by decimating the original image resolution. When an initial match of the template is found, the resolution may be progressively restored to its original quality and the location of the MMA progressively refined by template matching at each resolution level.

Figure 6B:
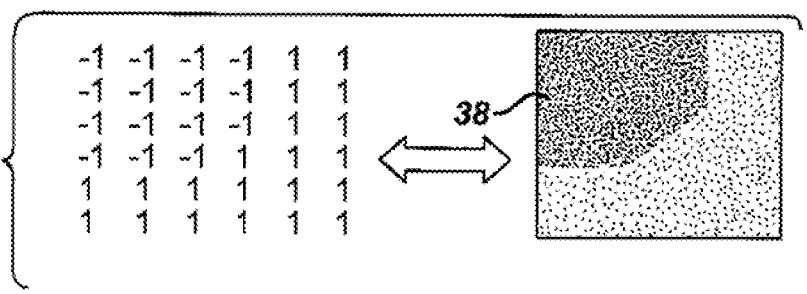

Once the MMA has been located a similar search is made for the location of the LMA, as shown in FIG. 3b. The small box 26 marks the location established for the MMA in the image 18, and a search area to the right of the MMA is defined as indicated by the box 34. A right corner geometric template, preferably a right octagon corner template 38 as shown in FIG. 6b, is matched by cross-correlation to the pixel values in the search area of box 34. Again, the image resolution may be decimated to speed the computational process and different template sizes may be used. The maximal correlation coefficient exceeding a predetermined threshold defines the location of the LMA.

Figure 7A:
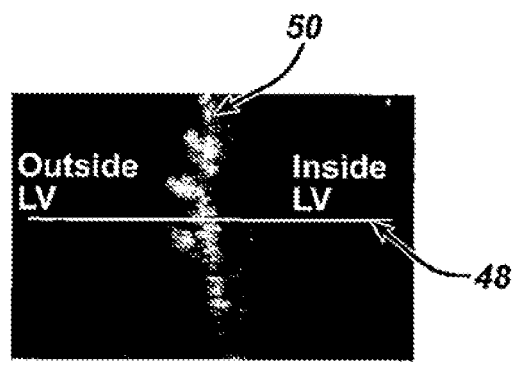
FIGS. 7a-7c illustrate a technique for fitting a standard border shape to the endocardial boundary of the LV.
Figure 7B:
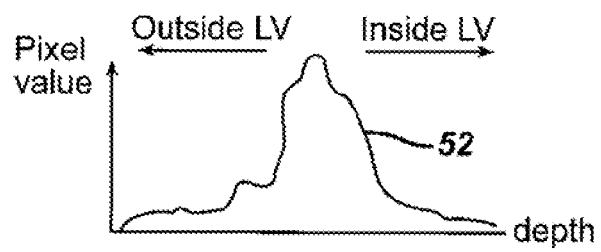
Figure 7C:
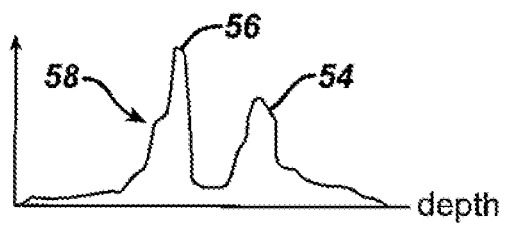

With the MMA 26 and the LMA 36 found, the next step in the process is to determine the position of the endocardial apex, which may be determined as shown in FIG. 4. The pixel values of the upper half of the septum 22 are analyzed to identify the nominal angle of the upper half of the septum, as indicated by the broken line 43. The pixel values of the lateral wall 42 of the LV are analyzed to identify the nominal angle of the upper half of the lateral wall 42, as shown by the broken line 45. If the lateral wall angle cannot be found with confidence, the angle of the scanlines on the right side of the sector is used. The angle between the broken lines 43,45 is bisected by a line 48, and the apex is initially assumed to be located at some point on this line. With the horizontal coordinate of the apex defined by line 48, a search is made of the slope of pixel intensity changes along the line 48 to determine the vertical coordinate of the apex. This search is made over a portion of line 48 which is at least a minimum depth and not greater than a maximum depth from the transducer probe, approximately the upper one-quarter of the length of line 48 above the mitral valve plane between the MMA 26 and the LMA 36. Lines of pixels along the line 48 and parallel thereto are examined to find the maximum positive brightness gradient from the LV chamber (where there are substantially no specular reflectors) to the heart wall (where many reflectors are located). A preferred technique for finding this gradient is illustrated in FIG. 7. FIG. 7a shows a portion of an ultrasound image including a section of the heart wall 50 represented by the brighter pixels in the image. Drawn normal to the heart wall 50 is a line 48 which, from right to left, extends from the chamber of the LV into and through the heart wall 50. If the pixel values along line 48 are plotted graphically, they would appear as shown by curve 52 in FIG. 7b, in which brighter pixels have greater pixel values. The location of the endocardium is not the peak of the curve 52, which is in the vicinity of the center of the heart wall, but relates to the sense of the slope of the curve. The slope of the curve 52 is therefore analyzed by computing the differential of the curve 52 as shown by the curve 58 in FIG. 7c. This differential curve has a peak 56 which is the maximal negative slope at the outside of the heart wall (the epicardium). The peak 54, which is the first major peak encountered when proceeding from right to left along curve 58, is the maximal positive slope which is the approximate location of the endocardium. The pixels along and parallel to line 48 in FIG. 4 are analyzed in this manner to find the endocardial wall and hence the location of the endocardial apex, marked by the small box 46 in FIG. 4.

If the user is operating on a sequence of stored images, the three points could be defined manually. For example, the user could point at the three landmarks in an image of the sequence with a pointing device such as a mouse or trackball, then click on them as they are identified to mark them in the image.

Once these three major landmarks of the LV have been located, one of a number of predetermined standard shapes for the LV is fitted to the three landmarks and the endocardial wall. Three such standard shapes are shown in FIGS. 5a, 5b, and 5c. The first shape, border 62, is seen to be relatively tall and curved to the left. The second shape, border 64, is seen to be relatively short and rounded. The third shape, border 66, is more triangular. Each of these standard shapes is scaled appropriately to fit the three landmarks 26,36,46. After an appropriately scaled standard shape is fit to the three landmarks, an analysis is made of the degree to which the shape fits the border in the echo data. This may be done, for example, by measuring the distances between the shape and the heart wall at points along the shape. Such measurements are made along paths orthogonal to the shape and extending from points along the shape. The heart wall may be detected using the operation discussed in FIGS. 7a-7c, for instance. The shape which is assessed as having the closest fit to the border to be traced, by an average of the distance measurements, for instance, is chosen as the shape used in the continuation of the protocol.

The chosen shape is then fitted to the border to be traced by "stretching" the shape, in this example, to the endocardial wall. The stretching is done by analyzing 48 lines of pixels evenly spaced around the border and approximately normal to heart wall. The pixels along each of the 48 lines are analyzed as shown in FIGS. 7a-7c to find the adjacent endocardial wall and the chosen shape is stretched to fit the endocardial wall. The baseline between points 26 and 36 is not fit to the shape but is left as a straight line, as this is the nominal plane of the mitral valve. When the shape has been fit to points along the heart wall, the border tracing is smoothed and displayed over the end systole image as shown in the image 78 on the right side of the dual display of FIG. 8. The display includes five control points shown as X's along the border between the MMA landmark and the apex, and five control points also shown as X's along the border between the apex landmark and the LMA landmark. In this example the portion of line 48 between the apex and the mitral valve plane is also shown, as adjusted by the stretching operation.

Figure 8:
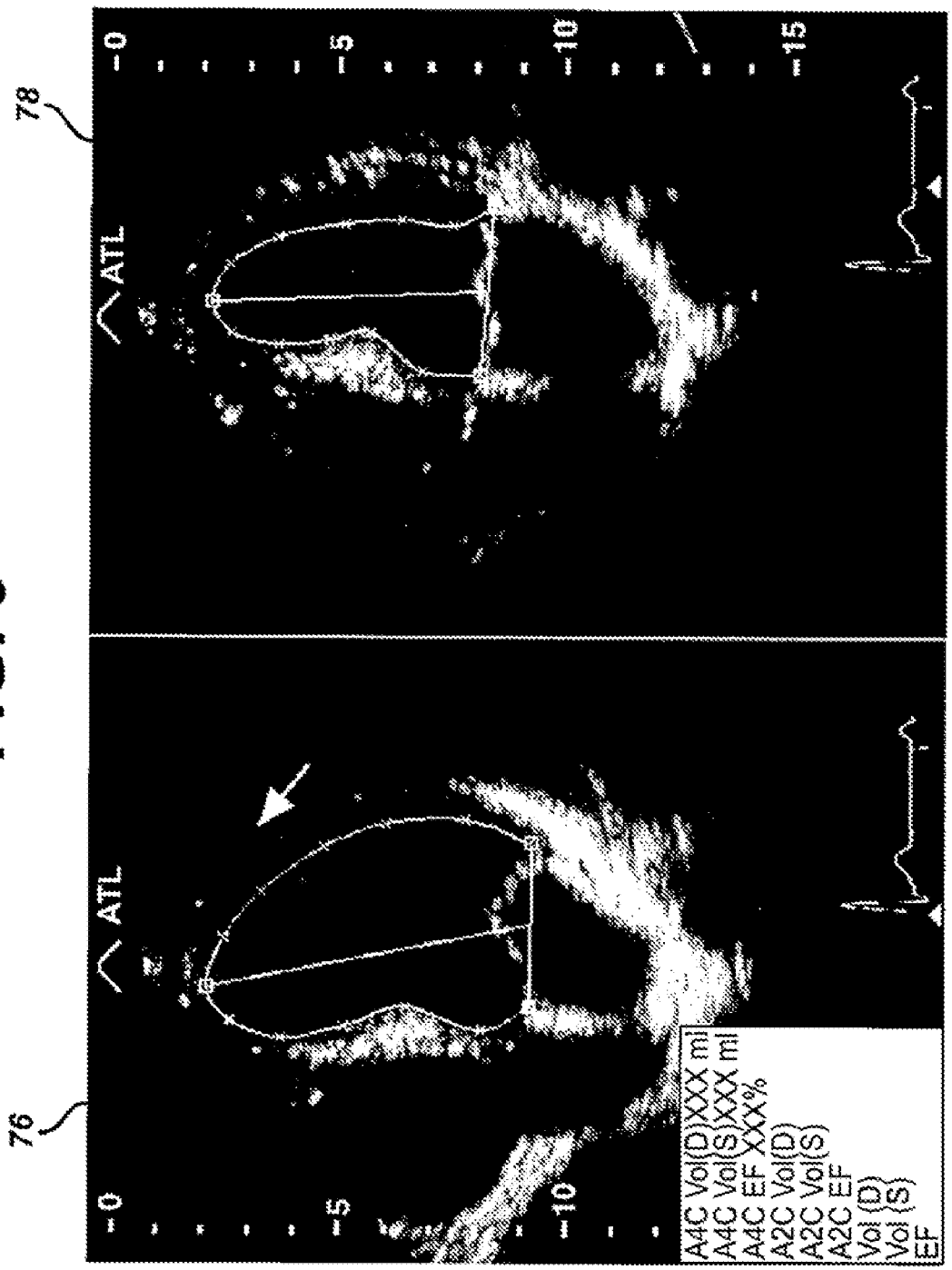
FIG. 8 illustrates an end diastole and end systole display with endocardial borders drawn automatically in accordance with the principles of the present invention.

Since each of the images shown in FIG. 8 is one image in a cardiac loop of images, the clinician can further verify the accuracy of the borders of the end diastole and end systole images 76,78 by playing a saved cardiac loop of images behind the borders drawn on the display of FIG. 8. This is done by selecting one of the images of FIG. 8, then selecting "Play" from the system menu to repetitively play the saved cardiac loop in real time or at a selected frame rate of display behind the border. In the end diastole image 76 the endocardium is at its maximum expansion; hence, the endocardium in the loop should appear to move inward from and then back to the endocardial border drawn on the end diastole image. In the end systole image 78 the endocardium is fully contracted; hence, the endocardium in the loop should appear to move outward and then back to the border in this image. If the endocardium does not move in this manner and, for example, is seen to pass through the border, a different image may need to be chosen for end diastole or end systole, or manual adjustment of a drawn border may be necessary. Of course, the loop and its drawn borders over the complete cardiac cycle can be replayed, enabling the clinician to view to endocardial tracing as it changes with the heart motion in real time.

Figure 9:
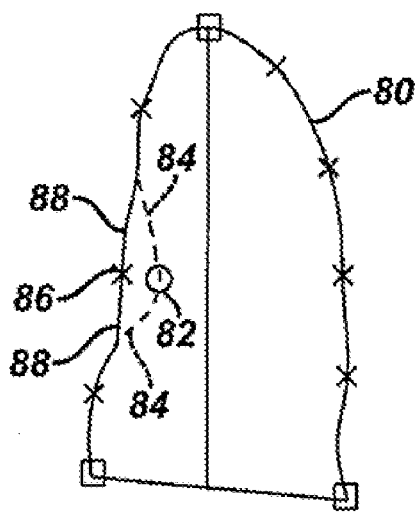
FIG. 9 illustrates the rubber-banding technique for adjusting an automatically drawn border.

Images with automatically traced borders which are saved in memory can be recalled and their automatically drawn borders refined by manual adjustment, if desired. This process is knows as "rubberbanding." As FIG. 8 shows, the endocardial borders of both the end diastole and end systole images have small boxes denoting the three major landmarks and control points marked by X's on the septal and lateral borders. The clinician chooses the default number of control point which will be displayed initially; on the border 80 shown in FIG. 9 there are three control points shown on the septal wall and four control points shown on the lateral wall. The clinician can review the end diastole and systole images, as well as all of the intervening images of the stored loop if desired, and manually adjust the positions of the landmark boxes and control point X's if it is seen that the automated process placed a border in an incorrect position. The clinician can slide a box or X along the border to a new position, and can add more control points or delete control points from the border. Suppose that the ABD processor had initially located the control point and border at the position shown by circle 82 and dashed line 84, which the clinician observes is incorrect. The clinician can relocate the control point laterally by dragging the X with a screen pointing device to the new location as shown by 86. As the X is dragged, the border moves or stretches along with the X, thereby defining a new border as shown by the solid line border 88. In this manner the clinician can manually correct and adjust the borders drawn by the ABD processor.

As the ABD processor is identifying the key landmarks and fitting borders to the sequence of images, it is periodically making confidence measurements to gauge the likelihood that the image borders are being accurately located and traced. For instance, if the septum is not clearly contrasted from the blood pool in the LV chamber, the automated process will stop. If the various correlation coefficients do not exceed predetermined thresholds the process will stop. Both spatial and temporal confidence measurements are employed. For instance, if the computed border of an image varies too much from a standard shape in either size or shape, the process will abort. This can arise if the landmarks are located in unusual positions in relation to each other, for example. If the change in the computed border from one image in the sequence to another is too great, the process will likewise abort. When the process stops, a message is displayed notifying the clinician of the reason for stopping the process, and gives the clinician the option to continue the automated process, to continue the automated process with or after clinician input, or for the clinician to acquire a new loop of images or manually trace the current images.

In the illustrated example of FIG. 8 the automatically drawn borders of the end diastole and end systole images are used to compute the heart's ejection fraction. This is done by an automatic modified Simpson's rule process which divides the delineated heart chamber at each phase into a stack of virtual disks. The diameter of each disk is used with the disk height to compute an effective volume of each disk, and these volumes are summed to compute the heart chamber volume at both end diastole and end systole. The difference between the two yields the ejection fraction, the volume or percentage of the heart volume which is expelled as pumped blood during each heart cycle. The ejection fraction calculation is shown in the measurement box at the lower left hand corner of FIG. 8 and is constantly updated. Thus, if the clinician should adjust a drawn border by the rubberbanding technique, the computed volume of the heart during that phase will change, affecting the ejection fraction calculation, and the new calculation immediately appears in the measurement box. As the clinician adjusts the drawn borders he instantaneously sees the effects of these changes on the calculation of the ejection fraction.

Figure 10:
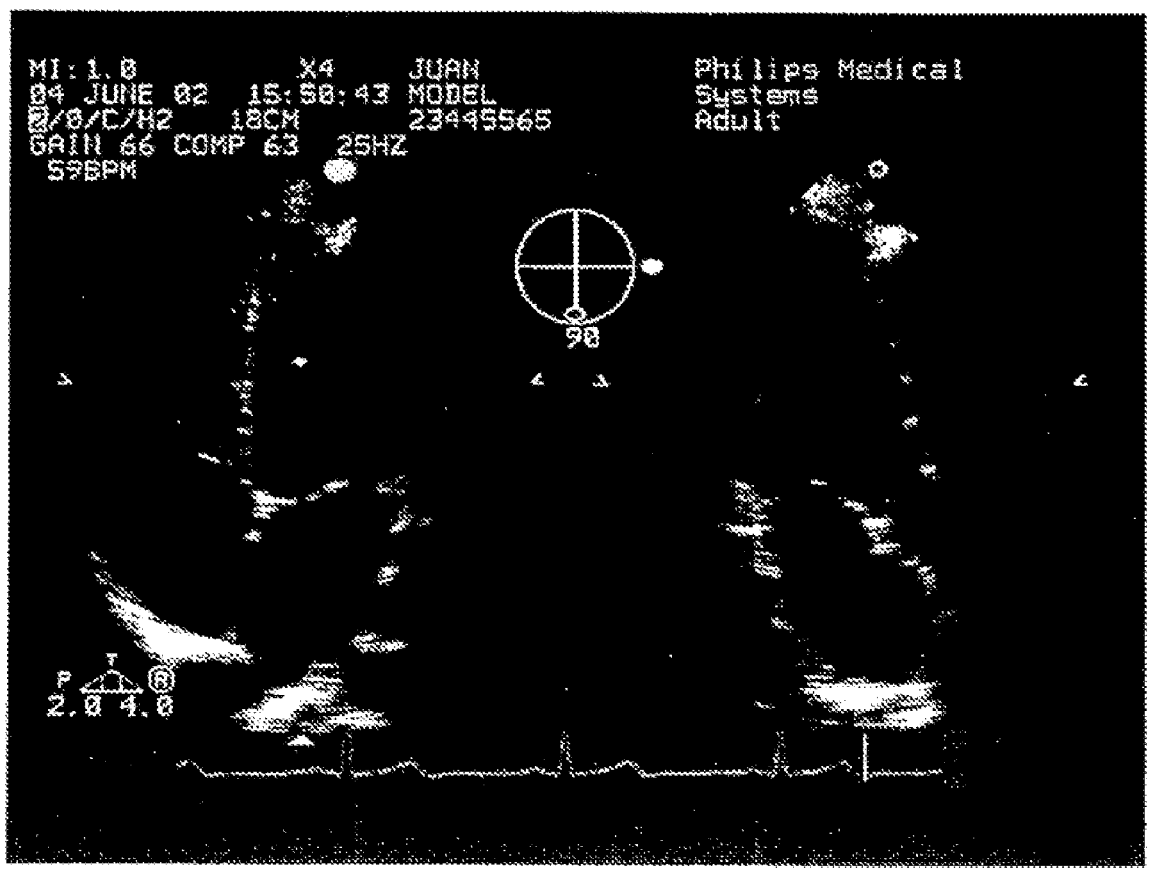
FIG. 10 is a photograph of an actual ultrasound system display when operating in the biplane mode in accordance with the principles of the present invention.

FIG. 10 illustrates biplane images which may be used in an embodiment of the present invention. As used herein the term "biplane images" refers to two images which are simultaneously acquired from different planes of a volumetric region of the body. Two images are acquired simultaneously when they are acquired in the same short time interval, which may be accomplished by acquiring the first and second images in rapid succession or by interleaved acquisition of scanlines from the two image planes until the two images have been fully acquired. US patent application Ser. No. 10/231,704; allowed, Jul. 28, 2003 entitled "BIPLANE ULTRASONIC IMAGING", incorporated herein by reference and of which I am a co-inventor describes two biplane modes. In the biplane implementation described in this patent, one image is acquired in a plane normal to the center of a two dimensional array transducer and the other image is initially in a plane centered with the first image but in a plane orthogonal to that of the first image. One of the images may then be relocated by either the "tilt" mode of operation or the "rotate" mode of operation. In the tilt mode, the second image is inclined to another image plane which intersects another scanline of the first image while remaining in an orthogonal orientation with the first image. The second image may be tilted from alignment with the center of the first image to alignment with the lateral scanlines of the first image or in alignment with any scanline between these extremes. In the rotate mode the two images retain their common centerline alignment but the second image plane is rotated about this centerline. The second image can be rotated from its initial orthogonal relationship with the first image to the same image plane as the first image, or at any rotation therebetween. FIG. 10 shows two biplane images in the rotate mode. The left image is a four-chamber heart image like those shown previously and the right image is orthogonal to the first and shows the left ventricle as it appears when intersected by the plane of the second image. The circular white icon between the two images in the center of the screen shows that the right image plane has been rotated ninety degrees from alignment with the left reference image plane. Marker dots are clearly visible in the icon and on the right sides of the apexes of the two sector images, indicating the left-right orientation of the two images. For completeness of a cardiac study the EKG trace is also shown below the biplane images.

An advantage of the present invention is that since only two planes of a volumetric region are being imaged, acquisition of the two images can be done rapidly enough so that the two images can both be real-time ultrasonic images at a relatively high frame rate of display. Moreover, the two images are of the heart at substantially the same point in time and are thus concurrently acquired images for purposes of the invention. A further advantage is that the ultrasound system need be only a conventional two dimensional imaging system. As FIG. 11 will illustrate, the display subsystem for biplane imaging can be a conventional two dimensional image processing subsystem, which means that biplane imaging in accordance with the present invention can be done with the two dimensional ultrasound systems currently in the hands of clinicians. The scanner and display subsystem of FIG. 11 needs no unique 3D capabilities in order to produce the biplane image shown in FIG. 10.

Figure 11:
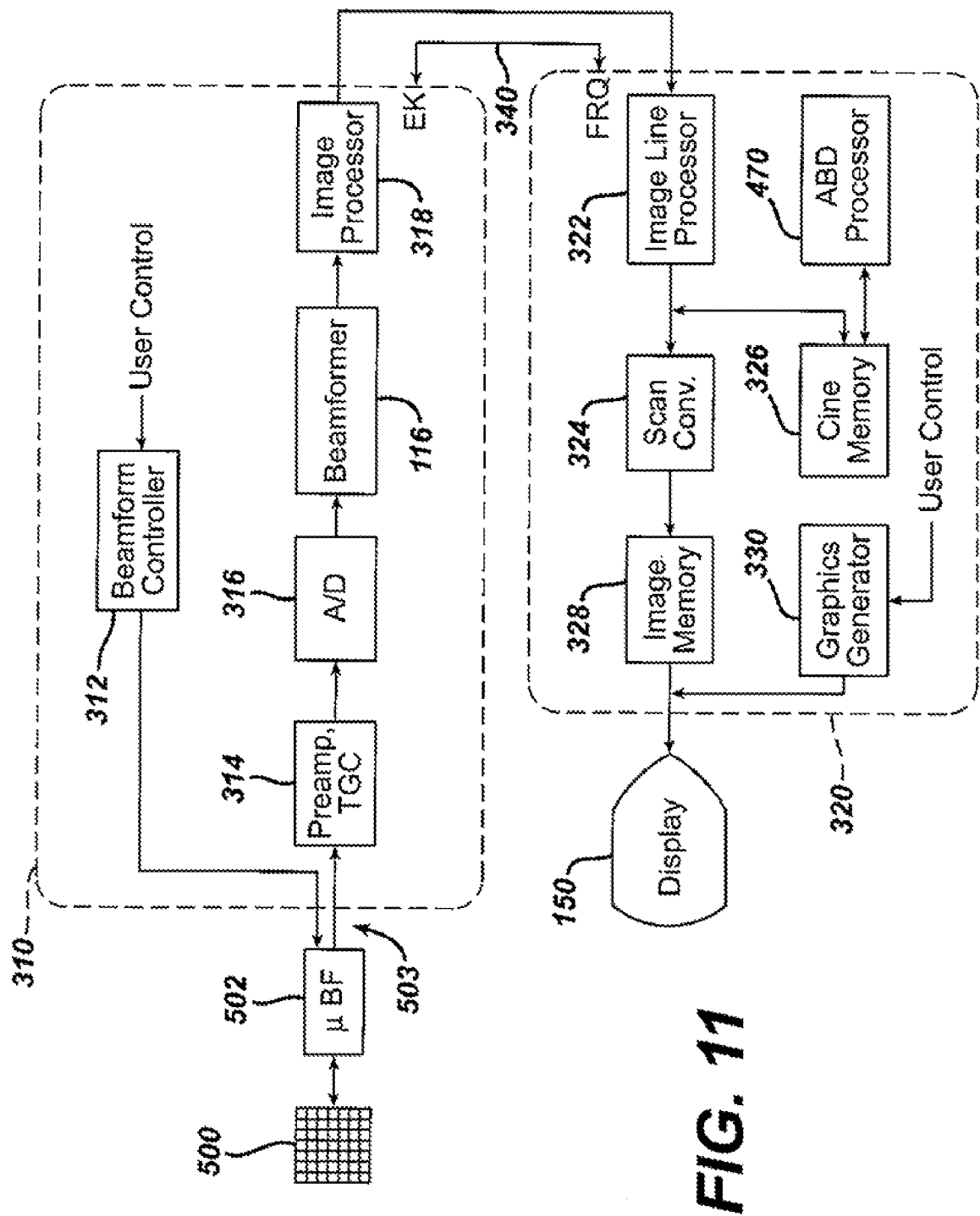
FIG. 11 illustrates in block diagram form an embodiment of an ultrasonic diagnostic imaging system constructed in accordance with the principles of the present invention.

Referring now to FIG. 11, an ultrasound system constructed in accordance with the principles of the present invention is shown in block diagram form. In this embodiment an ultrasound probe 110 includes a two dimensional array transducer 500 and a micro-beamformer 502. The micro-beamformer contains circuitry which controls the signals applied to groups of elements ("patches") of the array transducer 500 and does some processing of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control and provides control signals to the microbeamformer 502 instructing the probe as to the timing, frequency, direction and focusing of transmit beams. The beamform controller also control the beamforming of received echo signals by its coupling to the analog-to-digital (A/D) converters 316 and the beamformer 116. Echo signals received by the probe are amplified by preamplifier and TGC (time gain control) circuitry 314 in the scanner, then digitized by the A/D converters 316. The digitized echo signals are then formed into beams by a beamformer 116. The echo signals are then processed by an image processor 318 which performs digital filtering, B mode detection, and/or Doppler processing, and can also perform other signal processing such as harmonic separation, speckle reduction through frequency compounding, and other desired image processing.

The echo signals produced by the scanner 310 are coupled to a display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines of each biplane image are scan converted into the desired image format by a scan converter 324 which performs R-theta conversion as is known in the art. The images are then stored side-by-side (see FIG. 10) in an image memory 328 from which they can be displayed as one display frame on the display 150. The images in memory are also overlayed with graphics to be displayed with the images, which are generated by a graphics generator 330 which is responsive to a user control. Individual image frames or image frame sequences can be stored in a cine memory 326 during capture of image loops.

For real-time volumetric imaging the display subsystem 320 also includes the 3D image rendering processor 162 which receives image lines from the image line processor 322 for the rendering of a real-time three dimensional image which is displayed on the display 150.

Figure 12:
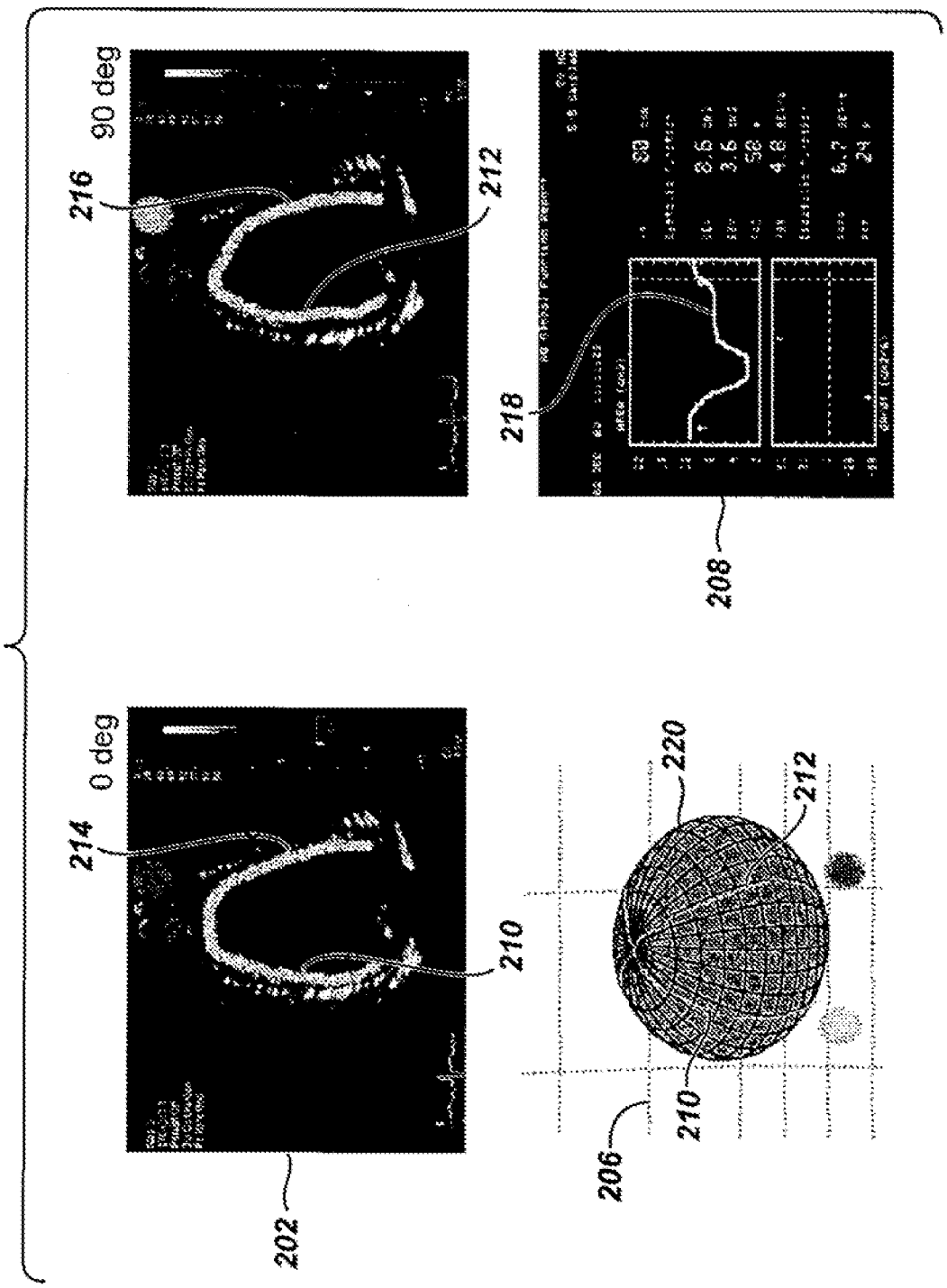
FIG. 12 illustrates an ultrasound display screen produced in accordance with the principles of the present invention.

In accordance with the principles of the present invention, the biplane system includes an automatic border detection (ABD) processor 470 which operates as described above in real time to automatically trace the myocardial borders of the biplane images as they are produced. The result of border tracing of orthogonal biplane LV images is shown in the user display of FIG. 12 which is that of a constructed embodiment of the present invention. In the embodiment of FIG. 12, the display screen is divided into four quadrants. In the upper left quadrant one of the biplane images is shown with the heart walls (endocardium 210 and epicardium 214) delineated by automatically drawn traces produced by the ABD processor and overlaid over the ultrasound image by the graphics generator 330. The orientation of the image plane of the ultrasound image in quadrant 202 is seen to be zero degrees.

A biplane image in a 90° orthogonal plane is shown in the upper right quadrant 204. Like the first biplane image, the epicardium 216 and endocardium 212 of the LV have been delineated by automatically drawn borders.

A graphical model of the LV chamber volume produced as an interpolated surface spline 220 is shown in the lower left quadrant 206 of the display. This surface spline is formed in this embodiment by fitting a surface to the orthogonal borders 210 and 212 as discussed below. The surface spline 220 encloses a volume which is measured by Simpson's formula (rule of disks) to estimate the instantaneous capacity of the LV at each time of biplane image acquisition. These quantitative volume measures are displayed as a function of time in the lower right quadrant 208 as illustrated by the physiologic curve 218 of the LV volume. Numeric measures of the volume at end diastole and end systole are shown to the right of the physiologic curve 218.

Figure 13A:
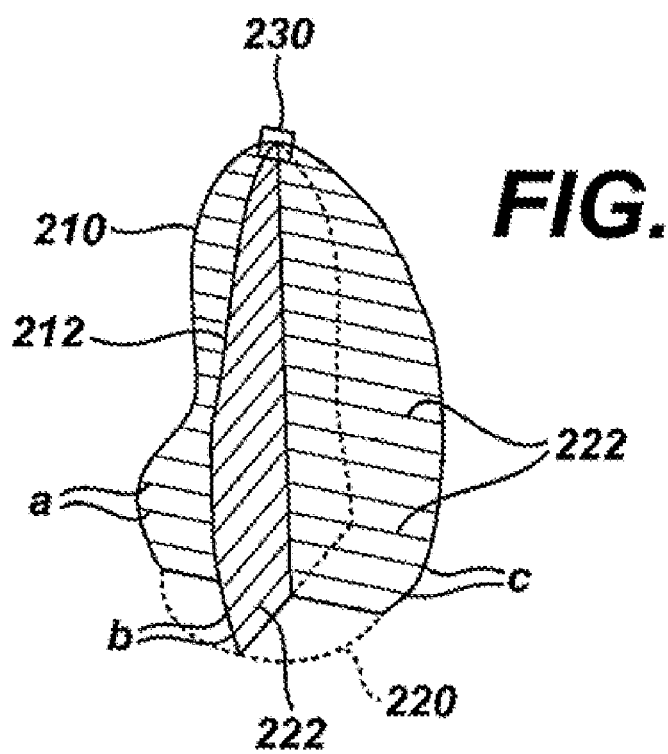
FIGS. 13a and 13b illustrate the formation of cavity segments from orthogonal views of the left ventricle.
Figure 13B:
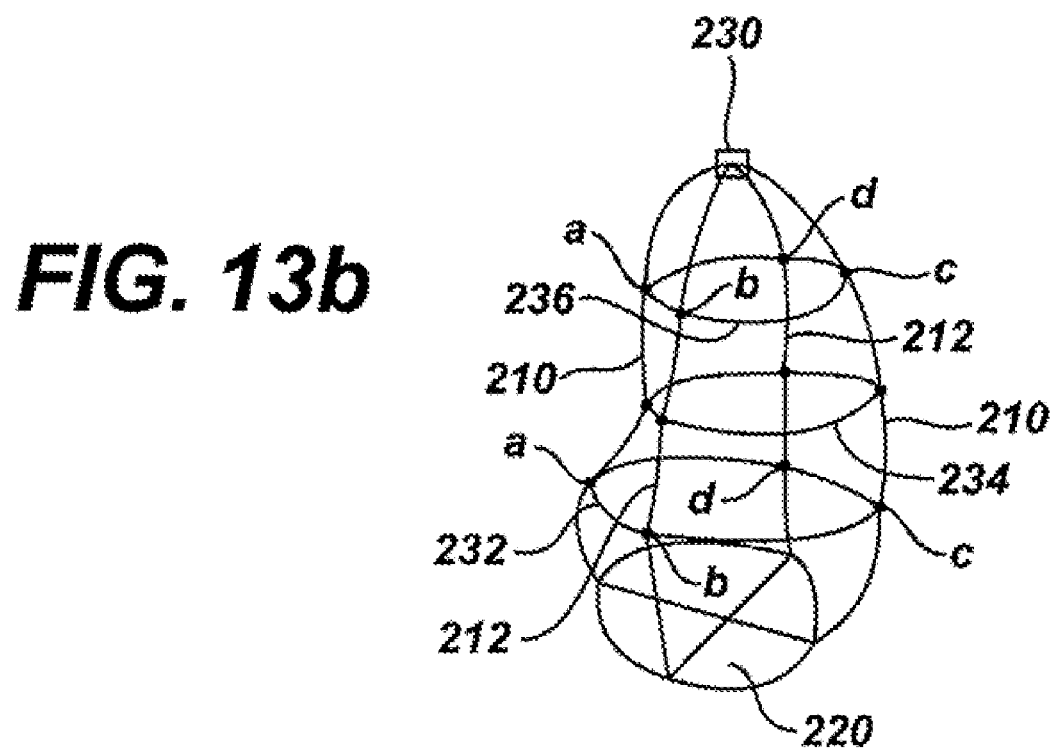

While various processes may be used to produce the spline surface 220 in FIG. 12, the technique used in a constructed embodiment is illustrated by FIGS. 13a and 13b. In the perspective view of FIG. 13a the two tracings 210 and 212 of the endocardial border of the simultaneous biplane images are shown on a base 220 which represents the mitral valve plane. The apex marker is shown at 230. In this example the image planes of the two biplane images are orthogonal to each other. The volume within the two tracings 210 and 212 is mathematically divided into spaced planes 222 which are parallel to the base plane 220. These planes intersect the left side of tracing 210 as shown at a,a and intersect the right side of tracing 210 as shown at c,c. The planes intersect the near side of tracing 212 as shown at b,b.

An ellipse is mathematically fit to the four intersection points a,b,c,d of each plane 222 as shown in FIG. 13b. While curves or splines other than ellipses can be used, including arcs and irregular shapes, an ellipse provides the advantage that Simpson's formula has been clinically validated when practiced with ellipses. FIG. 13b shows an ellipse 232 intersecting points a,b,c,d of the two tracings 210,212 near the base 220; an ellipse 234 intersecting the two tracings 210,212 toward the center of the LV volume; and an ellipse 236 intersecting the two tracings 210,212 near the top of the LV volume. When ellipses have been fit on each of the spaced planes 222, the disk-like volumes between the ellipses can be quantified by using the geometries of the adjacent ellipses and the distances between them. The total volume of all of the disk-like volumes is computed by summation to produce an instantaneous measure of the LV volume. The measure is used to produce another point on the physiologic curve 218 and, if the ECG waveform indicates that the heart is at end systole or end diastole, the appropriate numerical value is updated in the lower right quadrant 208 of the display.

In the constructed embodiment a surface is fit to the wire frame model of ellipses and tracings. This can be done by interpolating a surface that fits smoothly over the wire frame. The graphical model 220 of the cavity volume is then displayed with a continuous surface.

In operation, the display of the embodiment of FIG. 12 appears as follows. With the two dimensional array probe positioned to acquire biplane images intersecting in the vicinity of the apex of the LV, real time biplane images are displayed in the upper quadrants of the display. As each biplane image is acquired a corresponding border is traced on each image by the ABD processor 470 and displayed with the image. Each pair of time-concurrent tracings is used to produce an updated graphical volumetric model corresponding to the tracings of the biplane images at that point in time. An updated quantified volumetric measure of the LV is displayed graphically and/or numerically in the lower right quadrant of the display. As the LV borders of the ultrasound images and their tracings in quadrants 202 and 204 move inward and outward in real time, the graphical volumetric model 220 also swells and recedes correspondingly in real time, and the physiologic curve in the lower right quadrant scrolls in time as it is constantly updated.

It will be appreciated that other variations of the embodiments described above will readily occur to one skilled in the art. For instance, a wide variety of automatic or semi-automatic border detection processes may be used, including those described in U.S. Pat. No. 6,491,636 (Chenal et al.); U.S. Pat. No. 6,346,124 (Geiser et al.); and U.S. Pat. No. 6,106,465 (Napolitano et al.) While the biplane images in the example of FIG. 12 are shown in orthogonal planes, other planar orientations than 90° may be used. This may be done, for instance, after rotating one of the images as described in my aforementioned U.S. patent application Ser. No. 10/231,704; allowed, Jul. 28, 2003. Instead of using the images from two plane orientations, images from three or more intersecting planes can be acquired, traced, and used to display or quantify volumes or volume measures. Acquiring more images for each volume determination will be more time consuming but can produce a more anatomically accurate model of the cavity and more accurate volume measurements. Volumes can be defined globally or regionally. For instance, subregions on opposite sides of the LV can be defined by hemi-ellipses or splines and their volumes measured. Volumes which change over time can be identified and measured such as those produced by color kinesis. The volume of interest may be scanned using either a 2D matrix array transducer or a mechanically rotating 1D array transducer. A variety of volume measures may be made, such as ejection fraction and cardiac output determinations. The inventive technique can be used to measure other volumetric objects in the body besides the heart, such as a suspected tumor or anatomy of a developing fetus.

What is claimed is:

1. A method for ultrasonically measuring a volume of a heart in real time comprising:
   repetitively acquiring ultrasonic images of the heart during a heart cycle in two intersecting image planes which extend through the heart in different directions at substantially the same time with an ultrasound probe;
   using an automated processor to define corresponding object borders in the ultrasonic images during the heart cycle;
   producing a plurality of quantified measures of the volume of the heart during the heart cycle from the defined object borders in the different directions; and
   displaying measures of a continuous change in the heart volume as the heart beats.

2. The method of claim 1, further comprising producing a graphical model of the volumetric object using the defined object borders; and wherein producing quantified measures further comprises producing quantified measures using the graphical model.

3. The method of claim 1, wherein displaying further comprises producing a display comprising real time images from the two intersecting image planes with a visually highlighted defined object border in each image and a quantified measure using the defined object border of the images.

4. The method of claim 3, wherein producing a display comprising a quantified measure further comprises producing a display of changes in the volumetric object as a function of time.

5. The method of claim 3, wherein the display of changes in the volumetric object as a function of time comprises a graphical display, a numerical display or both a graphical and numeric display.

6. The method of claim 1, wherein acquiring ultrasonic images comprises acquiring ultrasonic images of a chamber of the heart,
wherein the corresponding object borders comprise the wall of the chamber of the heart.

7. The method of claim 2, further comprising producing a display comprising real time images from the two intersecting image planes with a visually highlighted defined object border in each image, a real time graphical model using the defined object borders, and a quantified measure using the defined object border of the images.

8. The method of claim 2, wherein producing quantified measures further comprises using the graphical model to produce a volumetric measure by the rule of disks.

9. The method of claim 2, wherein producing a graphical model comprises fitting a series of curves to a wire frame structure formed by the defined object borders.

10. The method of claim 9, wherein the curves comprise ellipses or hemi-ellipses.

11. A method for ultrasonically measuring the a volume of a heart comprising:
acquiring a sequence of ultrasonic images of the heart in real time during a heart cycle in two intersecting image planes at substantially the same time with an ultrasound probe, the intersecting image planes extending in different directions through the heart volume;
using an automated processor to define corresponding object borders in the ultrasonic images during the heart cycle;
producing a real time graphical model of a volumetric region of the heart using the defined object borders; and
producing from the defined object borders a real time measure of a change in heart volume during the heart cycle.

12. The method of claim 11, wherein using an automated processor further comprises using an automated processor to automatically trace corresponding object borders in the ultrasonic images; and wherein producing a graphical model comprises producing a wireframe model by fitting a series of curves to the traces in their corresponding image planes.

13. The method of claim 12, wherein the series of curves further comprise a series of ellipses.

14. The method of claim 12, wherein producing a graphical model further comprises fitting a surface to the wireframe model.

15. The method of claim 12, wherein producing a real time measure further comprises producing quantified measures of the graphical model by the rule of disks.

16. The method of claim 11, further comprising producing a display comprising real time images from the two intersecting image planes with a visually highlighted defined object border in each image and a real time graphical model using the defined object borders.

17. The method of claim 11, wherein acquiring comprises acquiring ultrasonic images of the volumetric object in two or more intersecting image planes at substantially the same time with an ultrasound probe.

* * * * *